(12) United States Patent
Bothra et al.

(10) Patent No.: US 12,243,630 B2
(45) Date of Patent: Mar. 4, 2025

(54) DRUG ALTERNATIVE RECOMMENDATION ENGINE FOR REAL-TIME PRESCRIPTION BENEFIT REQUESTS

(71) Applicant: Evernorth Strategic Development, Inc., St. Louis, MO (US)

(72) Inventors: Amit K. Bothra, Wildwood, MO (US); Aanal Patel, Bridgewater, NJ (US); Daniel C. Casper, Ellisville, MO (US); Pritesh J. Shah, Paramus, NJ (US); Jonelle Lofton, Florissant, MO (US); John J. Felo, II, Pipersville, PA (US); Gaspar Reyes, Grapevine, TX (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 265 days.

(21) Appl. No.: 17/677,319

(22) Filed: Feb. 22, 2022

(65) Prior Publication Data

US 2023/0268044 A1     Aug. 24, 2023

(51) Int. Cl.
*G16H 20/10*     (2018.01)
*G06Q 40/08*     (2012.01)

(52) U.S. Cl.
CPC ............ *G16H 20/10* (2018.01); *G06Q 40/08* (2013.01)

(58) Field of Classification Search
CPC ........ G16H 20/10; G16H 40/20; G16H 70/40; G06Q 40/08
See application file for complete search history.

(56) References Cited

U.S. PATENT DOCUMENTS

| | | |
|---|---|---|
| 9,786,023 B2 | 10/2017 | Cohan |
| 10,331,858 B2 | 6/2019 | Miller |
| 10,475,140 B2 | 11/2019 | Patel |
| 10,748,227 B2 | 8/2020 | Drzewucki |
| 10,817,920 B2 | 10/2020 | Begley |
| 10,922,687 B2 | 2/2021 | Mahaffey |

(Continued)

FOREIGN PATENT DOCUMENTS

WO     WO-2021050893 A1 *  3/2021  ............. G06F 9/542

OTHER PUBLICATIONS

Tuncay, Prescribing Behavior of General Practitioners for Generic Drugs, Aug. 14, 2020, International Journal of Environmental Research and Public Health, pp. 1-13 (Year: 2020).*

*Primary Examiner* — Christopher L Gilligan
(74) *Attorney, Agent, or Firm* — Dickinson Wright PLLC

(57) ABSTRACT

A method includes receiving a prescription benefit request and identifying one or more covered alternative drugs. The method also includes identifying one or more additional alternative drugs based on at least one of the requested drug and determining whether the one or more additional alternative drugs includes at least one covered additional alternative drug. The method also includes determining, for each of the at least one covered additional alternative drug and the one or more covered alternative drugs, an alternative drug value. The method also includes identifying the at least one covered additional alternative drug and the one or more covered alternative drugs having a lowest alternative drug value and generating a request response indicating at least the alternative drug of the at least one covered additional alternative drug and the one or more covered alternative drugs having the lowest alternative drug value.

18 Claims, 7 Drawing Sheets

(56) References Cited

U.S. PATENT DOCUMENTS

| | | | |
|---|---|---|---|
| 11,514,137 B1* | 11/2022 | Kaye | G16H 20/10 |
| 11,663,669 B1* | 5/2023 | Greenblatt | G06Q 40/08 |
| | | | 705/3 |
| 11,676,692 B1* | 6/2023 | Arends | G06F 9/542 |
| | | | 705/3 |
| 11,741,548 B1* | 8/2023 | Salud | G16H 40/20 |
| | | | 705/2 |
| 2007/0067186 A1 | 3/2007 | Brenner | |
| 2007/0162184 A1* | 7/2007 | Pinney | G07F 11/165 |
| | | | 221/9 |
| 2009/0043612 A1* | 2/2009 | Szela, Jr. | G16H 10/40 |
| | | | 705/3 |
| 2013/0151281 A1 | 6/2013 | Kaburick | |
| 2014/0244288 A1 | 8/2014 | Goodman | |
| 2016/0034668 A1 | 2/2016 | Rourke | |
| 2016/0225096 A1 | 8/2016 | Wells | |
| 2017/0344724 A1 | 11/2017 | Nockley | |
| 2020/0160957 A1 | 5/2020 | Key | |
| 2020/0167879 A1 | 5/2020 | Patel | |
| 2020/0302445 A1 | 9/2020 | Docken | |
| 2021/0074401 A1 | 3/2021 | Bezdek | |

\* cited by examiner

DRUG ALTERNATIVE RECOMMENDATION ENGINE FOR REAL-TIME PRESCRIPTION BENEFIT REQUESTS

TECHNICAL FIELD

This disclosure relates to prescription benefit requests, and in particular to systems and methods for using a drug alternative recommendation engine for real-time prescription benefit requests.

BACKGROUND

Medications, such as prescription medications, over-the-counter medications, vitamins, supplements, and the like, are typically provided by a medication provider, such as a large volume pharmacy and the like. A healthcare professional, such as a physician, may write a various prescriptions for a patient to provide therapeutic treatment, using a medication associated with a prescription, for corresponding ailments of the patient. The healthcare professional may engage with an interface, such as an interface on a computing device, to generate the prescription. In many cases, the interface may be configured to electronically submit the prescription to a pharmacy.

A prescription may include non-generic and/or generic versions of a medication, which may include a therapeutic alternative to the non-generic version of the medication. Typically, the patient, using insurance, may have a lower co-pay or an overall lower out of pocket expense for a generic version of a medication relative to the corresponding non-generic version of the medication. As such, healthcare professionals may identify a generic version of a medication as a therapeutic alternative to the non-generic version of the medication in order to reduce the healthcare expenses of the patient.

SUMMARY

This disclosure relates generally to real-time prescription benefit requests.

An aspect of the disclosed embodiments includes a system for identifying one or more alternative drugs responsive to a prescription benefits request. The system includes a processor and a memory. The memory includes instructions that, when executed by the processor, cause the processor to: receive a prescription benefit request, the prescription benefit request indicating at least a requested drug and a patient identifier; identify, in a first database, one or more covered alternative drugs based on the requested drug and a drug coverage plan associated with the patient identifier; identify, in a second database, one or more additional alternative drugs based on at least one of the requested drug and at least one covered alternative drug of the one or more covered alternative drugs; determine, based on the covered drug plan associated with the patient identifier, whether the one or more additional alternative drugs includes at least one covered additional alternative drug; in response to a determination that the one or more additional alternative drugs includes at least one covered additional alternative drug, determine, for each of the at least one covered additional alternative drug and the one or more covered alternative drugs, an alternative drug value; identify the at least one covered additional alternative drug and the one or more covered alternative drugs having a lowest alternative drug value; and generate a request response indicating at least the alternative drug of the at least one covered additional alternative drug and the one or more covered alternative drugs having the lowest alternative drug value.

Another aspect of the disclosed embodiments includes a method for identifying one or more alternative drugs responsive to a prescription benefits request. The method includes receiving a prescription benefit request, the prescription benefit request indicating at least a requested drug and a patient identifier and identifying, in a first database, one or more covered alternative drugs based on the requested drug and a drug coverage plan associated with the patient identifier. The method also includes identifying, in a second database, one or more additional alternative drugs based on at least one of the requested drug and at least one covered alternative drug of the one or more covered alternative drugs and determining, based on the covered drug plan associated with the patient identifier, whether the one or more additional alternative drugs includes at least one covered additional alternative drug. The method also includes, in response to a determination that the one or more additional alternative drugs includes at least one covered additional alternative drug, determining, for each of the at least one covered additional alternative drug and the one or more covered alternative drugs, an alternative drug value. The method also includes identifying the at least one covered additional alternative drug and the one or more covered alternative drugs having a lowest alternative drug value and generating a request response indicating at least the alternative drug of the at least one covered additional alternative drug and the one or more covered alternative drugs having the lowest alternative drug value.

Another aspect of the disclosed embodiments includes a system for identifying one or more alternative drugs responsive to a prescription benefits request. The system includes a processor and a memory. The memory includes instructions that, when executed by the processor, cause the processor to: receive a prescription benefit request, the prescription benefit request indicating at least a requested drug and a patient identifier; identify, in a first database, one or more covered alternative drugs based on the requested drug and a drug coverage plan associated with the patient identifier; identify, in a second database, one or more additional alternative drugs based on at least one of the requested drug and at least one covered alternative drug of the one or more covered alternative drugs; determine, based on the covered drug plan associated with the patient identifier, whether the one or more additional alternative drugs includes at least one covered additional alternative drug; in response to a determination that the one or more additional alternative drugs includes at least one covered additional alternative drug, determine, for each of the at least one covered additional alternative drug and the one or more covered alternative drugs, an alternative drug value; identify the at least one covered additional alternative drug and the one or more covered alternative drugs having a lowest alternative drug value; determine a dosage and frequency of the at least one covered additional alternative drug and the one or more covered alternative drugs having the lowest alternative drug value based on a dosage and frequency of the requested drug indicated by the prescription benefit request; and generate a request response indicating at least the alternative drug of the at least one covered additional alternative drug and the one or more covered alternative drugs having the lowest alternative drug value, the alternative drug value associated with the at least one covered additional alternative drug and the one or more covered alternative drugs having the lowest alternative drug value, and the dosage and frequency of the at least one covered additional alternative drug and the one or more covered alternative drugs having the lowest alternative drug value.

These and other aspects of the present disclosure are disclosed in the following detailed description of the embodiments, the appended claims, and the accompanying figures.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1A:
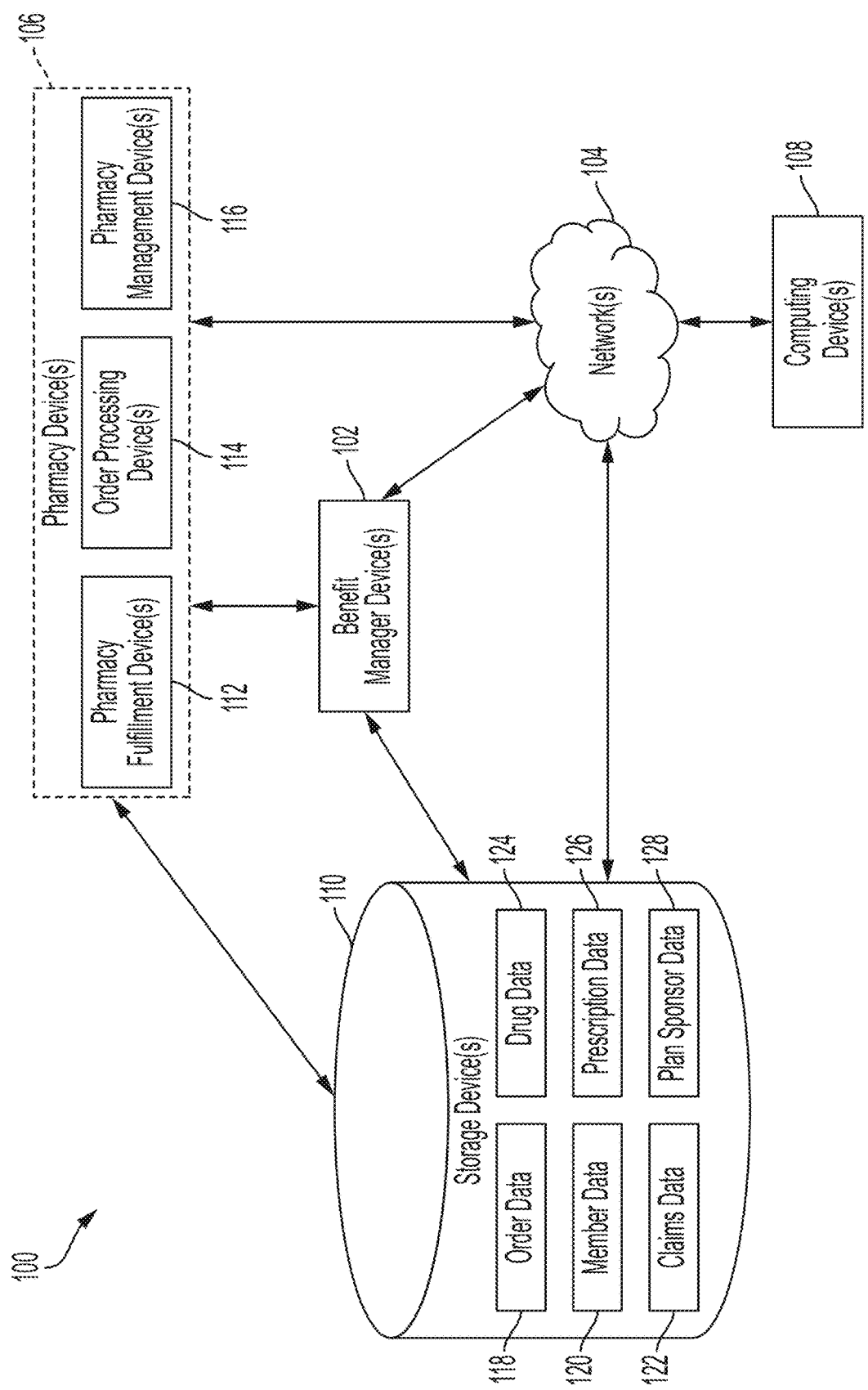
FIG. 1A generally illustrates a functional block diagram of a system including a high-volume pharmacy according to the principles of the present disclosure.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

As described, medications, such as prescription medications, over-the-counter medications, vitamins, supplements, and the like, are typically provided by a medication provider, such as a large volume pharmacy and the like. A healthcare processional, such as a physician, may write a various prescriptions for a patient to provide therapeutic treatment, using a medication associated with a prescription, for corresponding ailments of the patient. The healthcare professional may engage with an interface, such as an interface on a computing device (e.g., which may be part of an electronic prescription workflow (EPW) system), to generate the prescription. In many cases, the interface may be configured to electronically submit the prescription to a pharmacy.

A prescription may include non-generic and/or generic versions of a medication, which may include a therapeutic alternative to the non-generic version of the medication. Typically, the patient, using insurance, may have a lower co-pay or an overall lower out of pocket expense for a generic version of a medication relative to the corresponding non-generic version of the medication. As such, healthcare professionals may identify a generic version of a medication as a therapeutic alternative to the non-generic version of the medication in order to reduce the healthcare expenses of the patient.

Typically, as the healthcare professional interacts with the EPW system, the EPW system may invoke various application programming interfaces (APIs). For example, the healthcare professional may access the EPW system to generate a prescription for a patient. The EPW system may generate a real-time prescription benefit requests (RTPB) in response to the healthcare professional generating the prescription. The healthcare professional may provide, at one or more inputs, patient information (e.g., such as identification information), prescription information (e.g., such as medication or drug identification information, dosing information, frequency information, and the like), and/or other suitable information. The EPW system may generate the RTPB request based on such information.

As such, the RTPB may include a request for a patient cost for a drug associated with the RTPB request and/or a request for a formulary alternative for the drug (e.g., which may be referred to herein as an alternative drug) associated with the RTPB request. The EPW system ay invoke a price quote API in response to the request for the patient cost for the drug and/or a request for the alternative drugs. The price quote API may receive, from a first database, formulary alternatives for each trade name drug provided by the price quote API (e.g., from the RTPB request). The first database may include any suitable database and/or data structure. The first database may be referred to herein as a drug entity database, and/or a covered alternatives database.

In response to receiving the response from the first database (e.g., including the formulary alternatives), the price quote API may determine, based on a drug coverage plan (e.g., which may be part of a healthcare insurance plan) associated with the patient, whether each of the alternative drugs is covered under the drug coverage plan. Additionally, or alternatively, the price quote API may calculate a copayment responsibility (e.g., which may be referred to as a copay) for the patient for each alternative drug covered under the drug coverage plan. The price quote API may generate and provide a response to the RTPB request indicating one or more alternative drugs covered under the drug coverage plan and a corresponding copy, for each drug indicated by the RTPB request.

As healthcare professionals continue to prescribe such medications to patients, and as patients continue to use insurance to obtain the mediations, vast amounts of information is generated associated with the prescriptions (e.g., the type of medication prescribed, the dosing guidelines associated with the prescription, the treatment purpose for the medication, and the like), the insurance policy or plan, drug coverage plan, or documents used to obtain the prescriptions, the patient, the healthcare professional associated with the prescription, and the like. This may be referred to as big data and may be useful in identifying trends, averages, and the like.

Accordingly, systems and methods, such as those described herein, configured to identify additional alternative drugs using such big data to identify commonly prescribed alternatives and/or commonly filled drugs for prescriptions, may be desirable. In some embodiments, the systems and methods described herein may be configured to utilize commonly prescribed alternatives to provide more alternatives with a relatively higher frequency for RTPB requests.

The systems and methods described herein may be configured to provide a recommendation engine configured to suggest alternatives for incoming RTPB requests. The systems and methods described herein may be configured to use a learning algorithm to train he recommendation engine. The learning algorithm may include any suitable machine learning model or other suitable artificial intelligence developed using historical RTPB request data and/or actual filled claims.

In some embodiments, the systems and methods described herein may be configured to, for healthcare professionals using RTPB requests, provide all lower cost alternative medications for a prescribed drug. The systems and methods described herein may be configured to derive the lower cost medications from artificial intelligence utilizing one or more algorithms or machine learning models to make intelligent recommendations on drug options that reduce the financial responsibility of the patient.

In some embodiments, the systems and methods described herein may be configured to receive an RTPB request. The RTPB request may indicate at least a requested drug and a patient identifier (e.g., such as a group number policy number, and the like identifying the patient and/or a healthcare insurance plan and/or an associated drug coverage plan). The systems and methods described herein may be configured to identify, in a first database, one or more covered alternative drugs based on the requested drug and a drug coverage plan associated with the patient identifier.

The systems and methods described herein may be configured to identify, in a second database, one or more additional alternative drugs based on at least one of the requested drug and at least one covered alternative drug of the one or more covered alternative drugs. The second database may include any suitable database or data structure and may be referred to herein as an alternative table, an alternative drug database, and the like. The systems and methods described herein may be configured to populate the second database using historical prescribing data. For example, the systems and methods described herein may be configured to retrieve prior prescription benefit requests from one or more data sources having request dates within a first predetermined period (e.g., such as 1 year, 2 years, or other suitable period). The systems and methods described herein may be configured to identify, for each request of the prior prescription benefit requests, alternative drugs filled within a second predetermined period (e.g., 45 days, 60 days, 90 days, or other suitable period) of respective request dates associated with each request of the prior prescription benefit requests.

In some embodiments, the systems and methods described herein may be configured to, for each alternative drug filled within the second predetermined period of respective request dates associated with each request of the prior prescription benefit requests that includes a standard therapeutic class corresponding to a standard therapeutic class of a requested drug of a corresponding prior prescription benefit request, retrieve filled claim information associated with the corresponding prior prescription benefit requests. The systems and methods described herein may be configured to order or sort the alternative drugs by filled claims utilization indicated by the filled claim information.

In some embodiments, the systems and methods described herein may be configured to assign a therapeutic alternative flag to an alternative drug in response to a generic code number of the alternative drug matching a generic code number of a corresponding requested drug of a respective prior prescription benefit request. The systems and methods described herein may be configured to store, in the second database, at least each alternative drug that includes a standard therapeutic class corresponding to a standard therapeutic class of a requested drug of a corresponding prior prescription benefit request.

In some embodiments, the systems and methods described herein may be configured to determine, based on the covered drug plan associated with the patient identifier, whether the one or more additional alternative drugs includes at least one covered additional alternative drug. The systems and methods described herein may be configured to, in response to a determination that the one or more additional alternative drugs includes at least one covered additional alternative drug, determine, for each of the at least one covered additional alternative drug and the one or more covered alternative drugs, an alternative drug value. The alternative drug value may include a copay, out of pocket cost, a value contributing to reducing a deducible of the drug coverage plan, and the like.

The systems and methods described herein may be configured to identify the at least one covered additional alternative drug and the one or more covered alternative drugs having a lowest alternative drug value. The systems and methods described herein may be configured to generate a request response indicating at least the alternative drug of the at least one covered additional alternative drug and the one or more covered alternative drugs having the lowest alternative drug value. In some embodiments, the request response further indicates the alternative drug value associated with the at least one covered additional alternative drug and the one or more covered alternative drugs having the lowest alternative drug value.

In some embodiments, the systems and methods described herein may be configured to determine a dosage and frequency of the at least one covered additional alternative drug and the one or more covered alternative drugs having the lowest alternative drug value based on a dosage and frequency of the requested drug indicated by the prescription benefit request. In some embodiments, the request response further indicates the dosage and frequency of the at least one covered additional alternative drug and the one or more covered alternative drugs having the lowest alternative drug value.

FIG. 1A is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
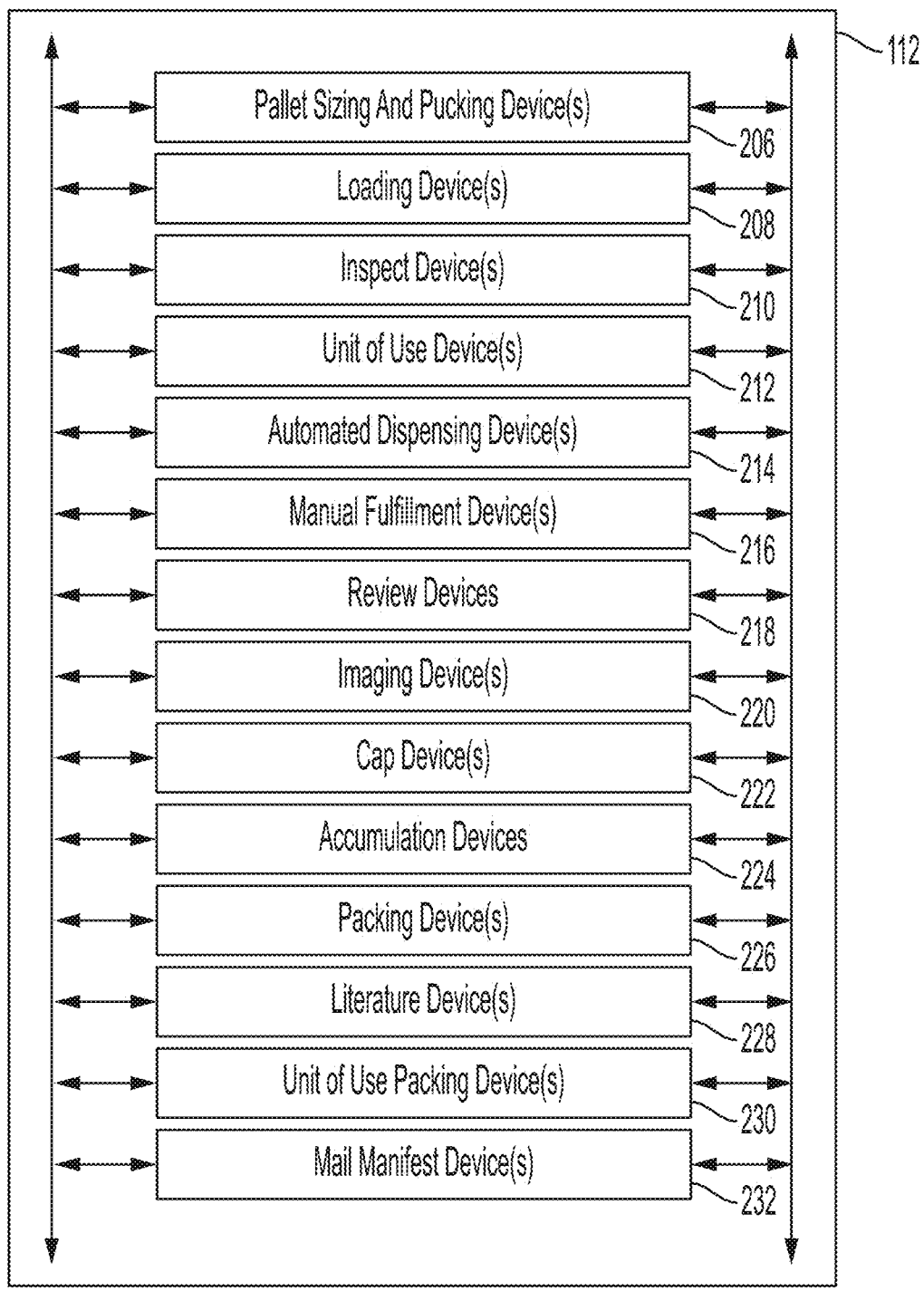
FIG. 2 generally illustrates a functional block diagram of a pharmacy fulfillment device, which may be deployed within the system of FIG. 1A.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model.

The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
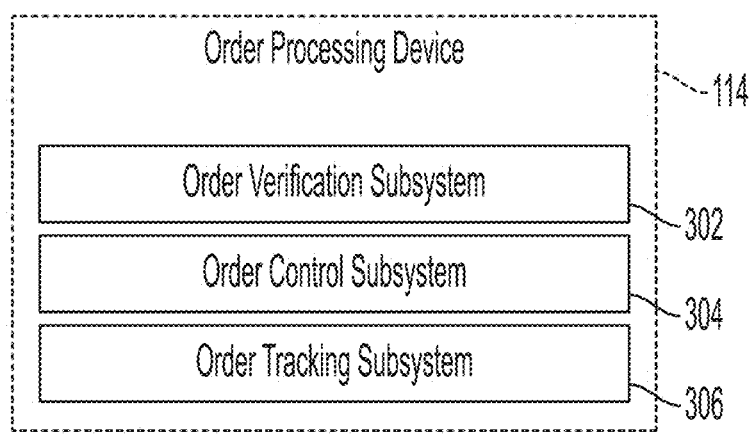
FIG. 3 generally illustrates a functional block diagram of an order processing device, which may be deployed within the system of FIG. 1A.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, and the like. The order tracking subsystem 306 may store data locally (for example, in a memory) or as a portion of the order data 118 stored in the storage device 110.

Figure 1B:
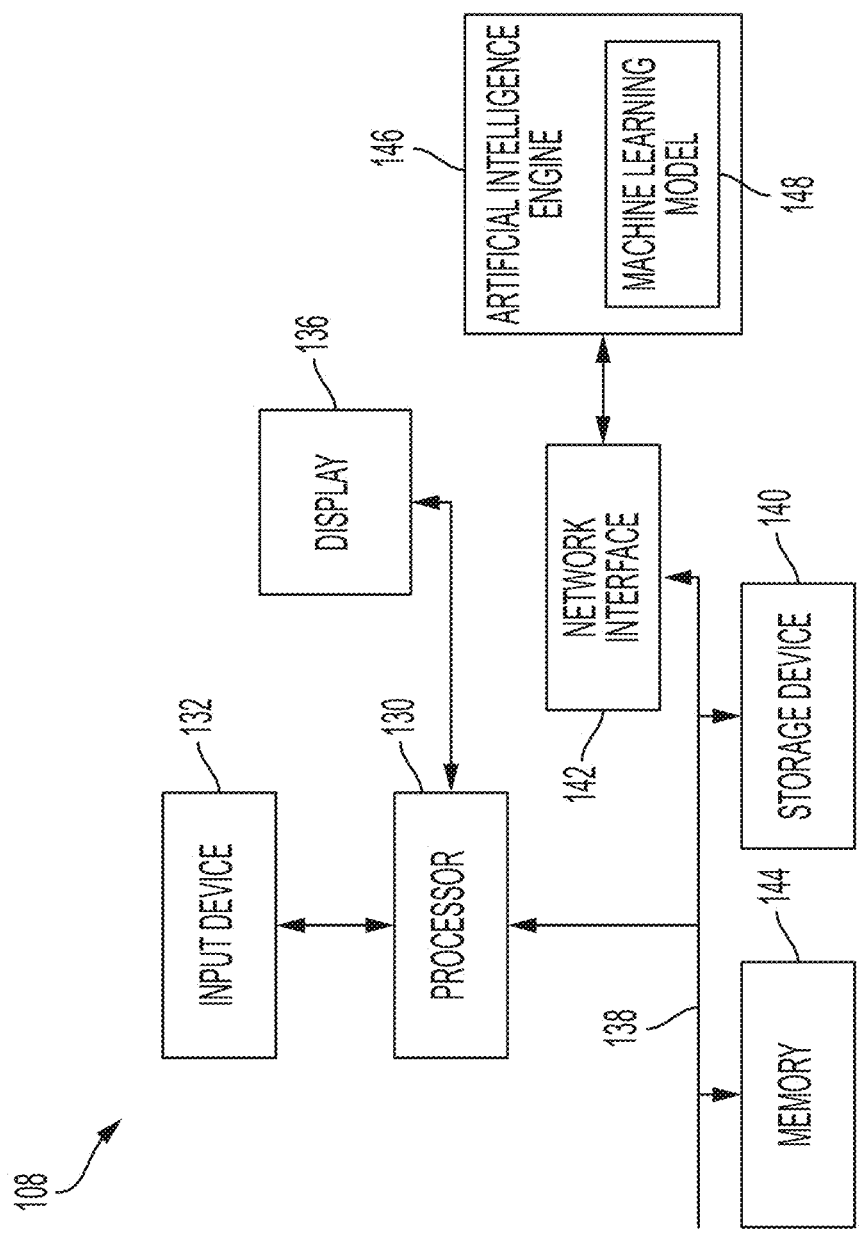
FIG. 1B generally illustrates a computing device according to the principles of the present disclosure.

In some embodiments, the system 100 may include one or more computing devices 108, as is generally illustrated in FIG. 1B. The computing device 108 may include any suitable computing device, such as a mobile computing device, a desktop computing device, a laptop computing device, a server computing device, other suitable computing device, or a combination thereof. The computing device 108 may be used by a user accessing the pharmacy associated with the system 100, as described. Additionally, or alternatively, the computing device 108 may be configured to identify an optimum or substantially optimum combination of data objects, as described.

The computing device 108 may include a processor 130 configured to control the overall operation of computing device 108. The processor 130 may include any suitable processor, such as those described herein. The computing device 108 may also include a user input device 132 that is configured to receive input from a user of the computing device 108 and to communicate signals representing the input received from the user to the processor 130. For example, the user input device 132 may include a button, keypad, dial, touch screen, audio input interface, visual/image capture input interface, input in the form of sensor data, etc.

The computing device 108 may include a display 136 that may be controlled by the processor 130 to display information to the user. A data bus 138 may be configured to facilitate data transfer between, at least, a storage device 140 and the processor 130. The computing device 108 may also include a network interface 142 configured to couple or connect the computing device 108 to various other computing devices or network devices via a network connection, such as a wired or wireless connection, such as the network 104. In some embodiments, the network interface 142 includes a wireless transceiver.

The storage device 140 may include a single disk or a plurality of disks (e.g., hard drives), one or more solid-state drives, one or more hybrid hard drives, and the like. The storage device 140 may include a storage management module that manages one or more partitions within the storage device 140. In some embodiments, storage device 140 may include flash memory, semiconductor (solid state) memory or the like. The computing device 108 may also include a memory 144. The memory 144 may include Random Access Memory (RAM), a Read-Only Memory (ROM), or a combination thereof. The memory 144 may store programs, utilities, or processes to be executed in by the processor 130. The memory 144 may provide volatile data storage, and stores instructions related to the operation of the computing device 108.

In some embodiments, the computing device 108 may use an artificial intelligence engine 146 configured to use at least one machine learning model 148 to perform the embodiments of systems and methods described herein. The artificial intelligence engine 146 may include any suitable artificial intelligence engine and may be disposed on computing device 108 or remotely located from the computing device 108, such as in a cloud computing device or other suitable remotely located computing device. The artificial intelligence engine 146 may use one or more machine learning models 148 to perform at least one of the embodiments disclosed herein. The computing device 108 may include a training engine capable of generating the one or more machine learning models 148. The machine learning models 148 may be trained to identify alternative drugs in response to RTPB requests and/or perform other suitable functions, as described.

Figure 4:
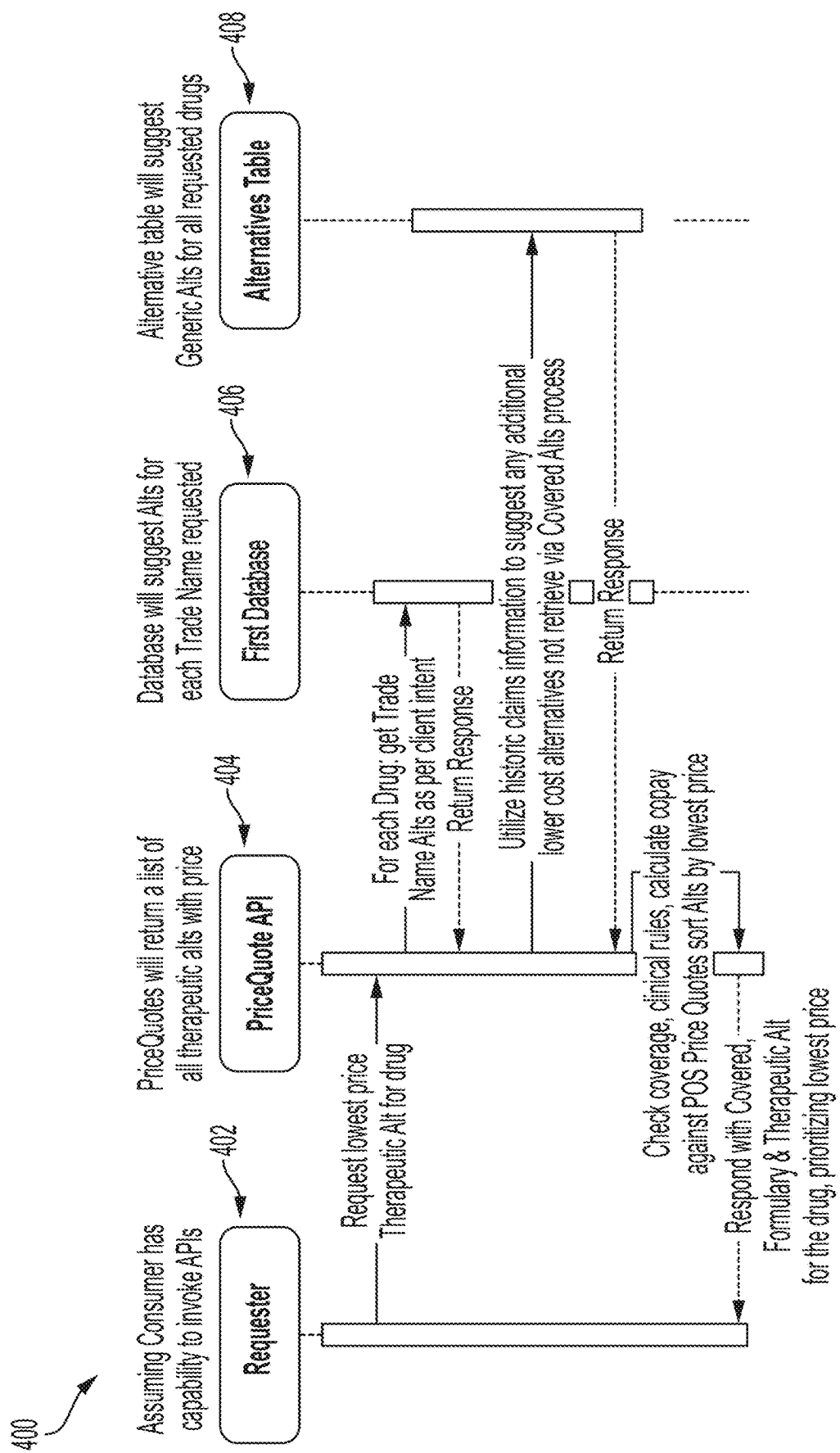
FIG. 4 generally illustrates real-time prescription benefit request data flow according to the principles of the present disclosure.

In some embodiments, the processor 130 may be configured to execute instructions stored on the memory 144 that cause the processor 130 and/or the computing device 108 to provide one or more recommended alternative drugs in response to RTPB requests. For example, as described, the healthcare professional (e.g., which may be referred to as a requester, such as the requester 402, as is generally illustrated in FIG. 4), may interact with the EPW system to generate one or more prescriptions for a patient. The requester 402 (e.g., which may include the healthcare professional and/or a computing device associated with the healthcare professional), may generate a RTPB request requesting a lowest price formulary (e.g., therapeutic) alternative (e.g., which may be referred to herein as an alternative drug) for a drug associated with the RTPB request.

The computing device 108 may be configured to invoke the price quote API 404. The price quote API 404 may be configured to provide, to a first database 406, for each drug indicated by the RTPB request, associated trade names (e.g., brand names and the like) and/or trade name alternatives (e.g., abbreviated trade names, other similar trade names, and the like).

The first database 406 may be configured to return a response indicating standard alternative drugs corresponding to each of the drugs provided by the price quote API 404. For example, the first database 406 may be populated with data indicating known and/or standard approved drug alternatives for each trade name drug.

The price quite API 404 may be configured to provide, to a second database 408 (e.g., which may be referred to in FIG. 4 as the alternatives table 408), for each drug indicated by the RTPB request, the associated trade names and/or the trade name alternatives. The second database 408 may be configured to utilize historic claims information to suggest or recommend any additional lower cost alternatives not indicated by the covered alternatives (e.g., the first database 406). The second database 406 may be configured to provide a response indicating the additional alternative dugs.

The price quote API 404 may check coverage of each of the alternative drugs provided by the first database 406 and the second database 408 using a drug coverage plan associated with the patient. The price quote API 404 may determine various clinical rules associated with each alternative drug. The price quote API 404 may determine a copay for each alternative drug based on the drug coverage plan. The price quote API 404 may sort the alternative drugs and identify the alternative drug associated with the lowest copay.

In some embodiments, the price quote API 404 may be configured to determine dose and frequency values for each alternative drug based on dose and frequency values associated with the requested drug. For example, the first database 406 and/or the second database 408 may include information correlating dose and frequency values for an alternative drug to dose and frequency values of the request drug. Additionally, or alternatively, the price quote API 404 may retrieve dose and frequency values for each alternative drug from any suitable source.

The price quote API 404 may generate and provide a response to the requester 402. The response may include covered alternative drugs, corresponding copays, dose values, frequency, values, other suitable information, or a combination thereof. The response may prioritize lower copay alternative drugs over higher copay alternative drugs.

In some embodiments, the computing device 108 may receive an RTPB request. The RTPB request may indicate at least a requested drug and a patient identifier (e.g., such as a group number policy number, and the like identifying the patient and/or a healthcare insurance plan and/or an associated drug coverage plan). The computing device 108 may identify, in the first database 406, one or more covered alternative drugs based on the requested drug and a drug coverage plan associated with the patient identifier.

The computing device 108 identify, in the second database 408, one or more additional alternative drugs based on at least one of the requested drug and at least one covered alternative drug of the one or more covered alternative drugs. The computing device 108 may populate the second database 408 using historical prescribing data. For example, the computing device 108 may retrieve prior prescription benefit requests from one or more data sources having request dates within a first predetermined period (e.g., such as 1 year, 2 years, or other suitable period). The computing device 108 may identify, for each request of the prior prescription benefit requests, alternative drugs filled within a second predetermined period (e.g., 45 days, 60 days, 90 days, or other suitable period) of respective request dates associated with each request of the prior prescription benefit requests.

The computing device 108 may, for each alternative drug filled within the second predetermined period of respective request dates associated with each request of the prior prescription benefit requests that includes a standard therapeutic class corresponding to a standard therapeutic class of a requested drug of a corresponding prior prescription benefit request, retrieve filled claim information associated with the corresponding prior prescription benefit requests.

The computing device 108 may order or sort the alternative drugs by filled claims utilization indicated by the filled claim information.

The computing device 108 may assign a therapeutic alternative flag to an alternative drug in response to a generic code number of the alternative drug matching a generic code number of a corresponding requested drug of a respective prior prescription benefit request. The computing device 108 may store, in the second database 408, at least each alternative drug that includes a standard therapeutic class corresponding to a standard therapeutic class of a requested drug of a corresponding prior prescription benefit request.

In some embodiments, the computing device 108 may determine, based on the covered drug plan associated with the patient identifier, whether the one or more additional alternative drugs includes at least one covered additional alternative drug. The computing device 108 may, in response to a determination that the one or more additional alternative drugs includes at least one covered additional alternative drug, determine, for each of the at least one covered additional alternative drug and the one or more covered alternative drugs, an alternative drug value. The alternative drug value may include a copay, out of pocket cost, a value contributing to reducing a deducible of the drug coverage plan, and the like.

The computing device 108 may identify the at least one covered additional alternative drug and the one or more covered alternative drugs having a lowest alternative drug value. The computing device 108 may generate a request response indicating at least the alternative drug of the at least one covered additional alternative drug and the one or more covered alternative drugs having the lowest alternative drug value. In some embodiments, the request response further indicates the alternative drug value associated with the at least one covered additional alternative drug and the one or more covered alternative drugs having the lowest alternative drug value.

In some embodiments, the computing device 108 may determine a dosage and frequency of the at least one covered additional alternative drug and the one or more covered alternative drugs having the lowest alternative drug value based on a dosage and frequency of the requested drug indicated by the prescription benefit request. In some embodiments, the request response further indicates the dosage and frequency of the at least one covered additional alternative drug and the one or more covered alternative drugs having the lowest alternative drug value.

In some embodiments, the order processing device 114 may receive, from the computing device 108 or other suitable computing device, an order associated with a prescription request to fill the alternative drug (e.g., including a corresponding dosage and frequency of the prescription for the alternative drug). The pharmacy fulfillment device 112 may fulfill, dispense, aggregate, and/or pack the order components of the alternative drug in accordance with one or more prescription orders directed by the order processing device 114.

In some embodiments, the computing device 108 and/or the system 100 may perform the methods described herein. However, the methods described herein as performed by the computing device 108 and/or the system 100 are not meant to be limiting, and any type of software executed on a computing device or a combination of various computing devices can perform the methods described herein without departing from the scope of this disclosure.

Figure 5:
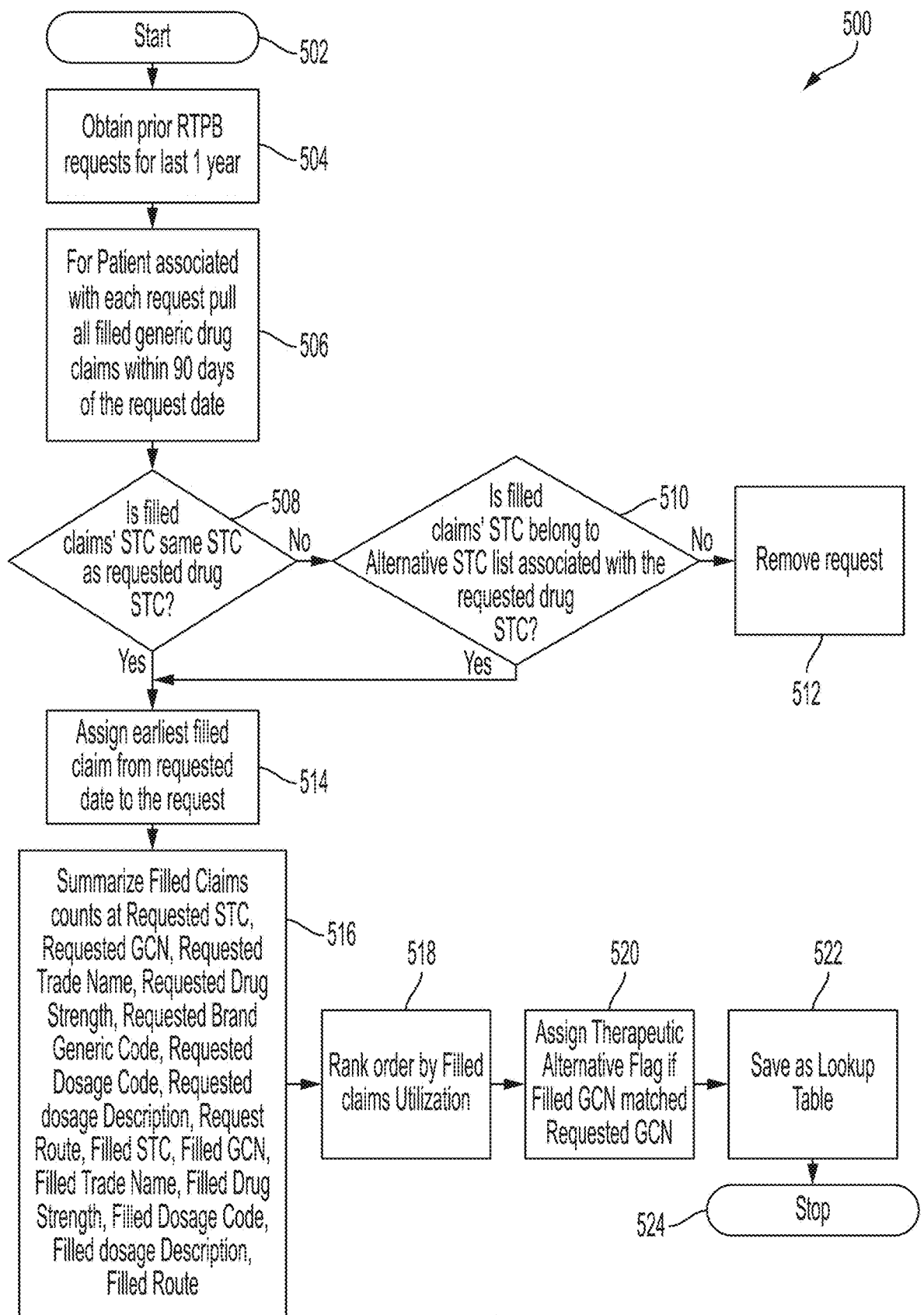
FIG. 5 is a flow diagram generally illustrating a drug alternative recommendation method according to the principles of the present disclosure.

FIG. 5 is a flow diagram generally illustrating a drug alternative recommendation method 500 according to the principles of the present disclosure. At 502, the method 500 begins. At 504, the method 500 obtained prior RTPB requests for a period of 1 year from a current date or other suitable date.

At 506, the method 500, for patients associated with each request, pulls all filled generic drug claims within 90 days of the request date (e.g., the request date on a corresponding request).

At 508, the method 500 determines whether a standard therapeutic class (STC) of a filled claim is the same as a STC as a corresponding requested drug. If the STC of the filled claim is not the same as the STC of the corresponding requested drug, the method 500 continues at 510. Alternatively, if the STC of the filled claim is the same as the STC of the corresponding requested drug, the method 500 continues at 514.

At 510, the method 500 determined whether the STC of the filled claim belongs to an alternative STC list associated with the STC of the corresponding requested drug. If the STC of the filled claim belongs to the alternative STC list associated with the STC of the corresponding requested drug, the method 500 continues at 514. Alternatively, if the STC of the filled claim does not belong to the alternative STC list associated with the STC of the corresponding requested drug, the method 500 continues at 512.

At 512, the method 500 removes the request.

At 514, the method 500 assigns an earliest filled claim from a corresponding requested date to the request.

At 516, the method 500 summarizes the filled claims. For example, the method 500 may summarize the filled claims by summarizing filled claims counts at requested STC, requested generic code number (GCN), requested trade name, requested drug strength, requested brand generic code, requested dosage code, requested dosage description, request route, filled STC, filled GNC, filled trade name, filled drug strength, filled dosage code, filled dosage description, filled route, other suitable information, or a combination thereof.

At 518, the method 500 rank orders the requests by filled claims utilization. For example, the method 500 may sort or rank the requests based on the number of times that a particular drug was filled.

At 520, the method 500 saves the alternative drugs associated with requests and/or other suitable information associated with the requests to a look up table.

At 524, the method 50 ends.

Figure 6:
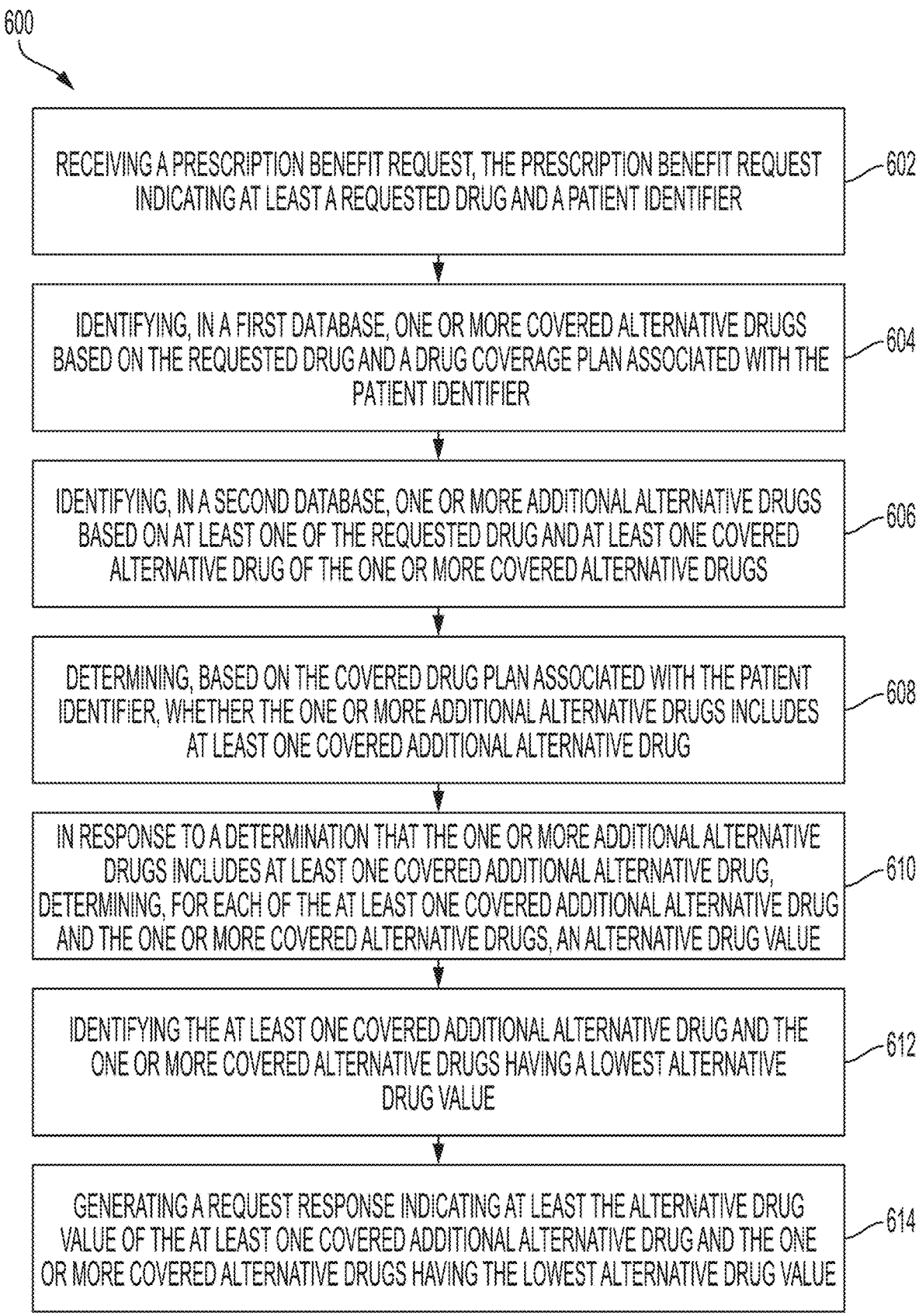
FIG. 6 is a flow diagram generally illustrating an alternative drug alternative recommendation method according to the principles of the present disclosure.

FIG. 6 is a flow diagram generally illustrating an alternative drug alternative recommendation method 600 according to the principles of the present disclosure. At 602, the method 600 receives a prescription benefit request. The prescription benefit request may indicate at least a requested drug and a patient identifier.

At 604, the method 600 identifies, in a first database, one or more covered alternative drugs based on the requested drug and a drug coverage plan associated with the patient identifier.

At 606, the method 600 identifies, in a second database, one or more additional alternative drugs based on at least one of the requested drug and at least one covered alternative drug of the one or more covered alternative drugs.

At 608, the method 600 determines, based on the covered drug plan associated with the patient identifier, whether the one or more additional alternative drugs includes at least one covered additional alternative drug.

At 610, the method 600, in response to a determination that the one or more additional alternative drugs includes at least one covered additional alternative drug, determines, for each of the at least one covered additional alternative drug and the one or more covered alternative drugs, an alternative drug value.

At 612, the method 600 identifies the at least one covered additional alternative drug and the one or more covered alternative drugs having a lowest alternative drug value.

At 614, the method 600 generates a request response indicating at least the alternative drug of the at least one covered additional alternative drug and the one or more covered alternative drugs having the lowest alternative drug value.

In some embodiments, a system for identifying one or more alternative drugs responsive to a prescription benefits request includes a processor and a memory. The memory includes instructions that, when executed by the processor, cause the processor to: receive a prescription benefit request, the prescription benefit request indicating at least a requested drug and a patient identifier; identify, in a first database, one or more covered alternative drugs based on the requested drug and a drug coverage plan associated with the patient identifier; identify, in a second database, one or more additional alternative drugs based on at least one of the requested drug and at least one covered alternative drug of the one or more covered alternative drugs; determine, based on the covered drug plan associated with the patient identifier, whether the one or more additional alternative drugs includes at least one covered additional alternative drug; in response to a determination that the one or more additional alternative drugs includes at least one covered additional alternative drug, determine, for each of the at least one covered additional alternative drug and the one or more covered alternative drugs, an alternative drug value; identify the at least one covered additional alternative drug and the one or more covered alternative drugs having a lowest alternative drug value; and generate a request response indicating at least the alternative drug of the at least one covered additional alternative drug and the one or more covered alternative drugs having the lowest alternative drug value.

In some embodiments, the request response further indicates the alternative drug value associated with the at least one covered additional alternative drug and the one or more covered alternative drugs having the lowest alternative drug value. In some embodiments, the instructions further cause the processor to determine a dosage and frequency of the at least one covered additional alternative drug and the one or more covered alternative drugs having the lowest alternative drug value based on a dosage and frequency of the requested drug indicated by the prescription benefit request. In some embodiments, the request response further indicates the dosage and frequency of the at least one covered additional alternative drug and the one or more covered alternative drugs having the lowest alternative drug value. In some embodiments, the instructions further cause the processor to retrieve prior prescription benefit requests having request dates within a first predetermined period, and identify, for each request of the prior prescription benefit requests, alternative drugs filled within a second predetermined period of respective request dates associated with each request of the prior prescription benefit requests. In some embodiments, the instructions further cause the processor to, for each alternative drug filled within the second predetermined period of respective request dates associated with each request of the prior prescription benefit requests that includes a standard therapeutic class corresponding to a standard therapeutic class of a requested drug of a corresponding prior prescription benefit request, retrieve filled claim information associated with the corresponding prior prescription benefit requests; and order the alternative drugs by filled claims utilization indicated by the filled claim information. In some embodiments, the instructions further cause the processor to assign a therapeutic alternative flag to an alternative drug in response to a generic code number of the alternative drug matching a generic code number of a corresponding requested drug of a respective prior prescription benefit request. In some embodiments, the instructions further cause the processor to store, in the second database, at least each alternative drug that includes a standard therapeutic class corresponding to a standard therapeutic class of a requested drug of a corresponding prior prescription benefit request. In some embodiments, the instructions further cause the processor to communicate an order associated with a prescription request to fill the alternative drug to an order processing device associated with a high-volume pharmacy, wherein the order processing device instructions a pharmacy fulfillment device to fulfill the order In some embodiments, a method for identifying one or more alternative drugs responsive to a prescription benefits request includes receiving a prescription benefit request, the prescription benefit request indicating at least a requested drug and a patient identifier and identifying, in a first database, one or more covered alternative drugs based on the requested drug and a drug coverage plan associated with the patient identifier. The method also includes identifying, in a second database, one or more additional alternative drugs based on at least one of the requested drug and at least one covered alternative drug of the one or more covered alternative drugs and determining, based on the covered drug plan associated with the patient identifier, whether the one or more additional alternative drugs includes at least one covered additional alternative drug. The method also includes, in response to a determination that the one or more additional alternative drugs includes at least one covered additional alternative drug, determining, for each of the at least one covered additional alternative drug and the one or more covered alternative drugs, an alternative drug value. The method also includes identifying the at least one covered additional alternative drug and the one or more covered alternative drugs having a lowest alternative drug value and generating a request response indicating at least the alternative drug of the at least one covered additional alternative drug and the one or more covered alternative drugs having the lowest alternative drug value.

In some embodiments, the request response further indicates the alternative drug value associated with the at least one covered additional alternative drug and the one or more covered alternative drugs having the lowest alternative drug value. In some embodiments, the method also includes determining a dosage and frequency of the at least one covered additional alternative drug and the one or more covered alternative drugs having the lowest alternative drug value based on a dosage and frequency of the requested drug indicated by the prescription benefit request. In some embodiments, the request response further indicates the dosage and frequency of the at least one covered additional alternative drug and the one or more covered alternative drugs having the lowest alternative drug value. In some embodiments, the method also includes retrieving prior prescription benefit requests having request dates within a first predetermined period, and identifying, for each request of the prior prescription benefit requests, alternative drugs filled within a second predetermined period of respective request dates associated with each request of the prior prescription benefit requests. In some embodiments, the method also includes, for each alternative drug filled within the second predetermined period of respective request dates associated with each request of the prior prescription benefit requests that includes a standard therapeutic class corresponding to a standard therapeutic class of a requested drug of a corresponding prior prescription benefit request, retrieving filled claim information associated with the corresponding prior prescription benefit requests, and ordering the alternative drugs by filled claims utilization indicated by the filled claim information. In some embodiments, the method also includes assigning a therapeutic alternative flag to an alternative drug in response to a generic code number of the alternative drug matching a generic code number of a corresponding requested drug of a respective prior prescription benefit request. In some embodiments, the method also includes storing, in the second database, at least each alternative drug that includes a standard therapeutic class corresponding to a standard therapeutic class of a requested drug of a corresponding prior prescription benefit request. In some embodiments, the method also includes communicating an order associated with a prescription request to fill the alternative drug to an order processing device associated with a high-volume pharmacy, wherein the order processing device instructions a pharmacy fulfillment device to fulfill the order In some embodiments, a system for identifying one or more alternative drugs responsive to a prescription benefits request includes a processor and a memory. The memory includes instructions that, when executed by the processor, cause the processor to: receive a prescription benefit request, the prescription benefit request indicating at least a requested drug and a patient identifier; identify, in a first database, one or more covered alternative drugs based on the requested drug and a drug coverage plan associated with the patient identifier; identify, in a second database, one or more additional alternative drugs based on at least one of the requested drug and at least one covered alternative drug of the one or more covered alternative drugs; determine, based on the covered drug plan associated with the patient identifier, whether the one or more additional alternative drugs includes at least one covered additional alternative drug; in response to a determination that the one or more additional alternative drugs includes at least one covered additional alternative drug, determine, for each of the at least one covered additional alternative drug and the one or more covered alternative drugs, an alternative drug value; identify the at least one covered additional alternative drug and the one or more covered alternative drugs having a lowest alternative drug value; determine a dosage and frequency of the at least one covered additional alternative drug and the one or more covered alternative drugs having the lowest alternative drug value based on a dosage and frequency of the requested drug indicated by the prescription benefit request; generate a request response indicating at least the alternative drug of the at least one covered additional alternative drug and the one or more covered alternative drugs having the lowest alternative drug value, the alternative drug value associated with the at least one covered additional alternative drug and the one or more covered alternative drugs having the lowest alternative drug value, and the dosage and frequency of the at least one covered additional alternative drug and the one or more covered alternative drugs having the lowest alternative drug value; and communicate an order associated with a prescription request to fill the alternative drug to an order processing device associated with a high-volume pharmacy, wherein the order processing device instructions a pharmacy fulfillment device to fulfill the order.

In some embodiments, the instructions further cause the processor to retrieve prior prescription benefit requests having request dates within a first predetermined period, and identify, for each request of the prior prescription benefit requests, alternative drugs filled within a second predetermined period of respective request dates associated with each request of the prior prescription benefit requests. In some embodiments, the instructions further cause the processor to, for each alternative drug filled within the second predetermined period of respective request dates associated with each request of the prior prescription that includes a standard therapeutic class corresponding to a standard therapeutic class of a requested drug of a corresponding prior prescription benefit request, retrieve filled claim information associated with the corresponding prior prescription benefit requests, and order the alternative drugs by filled claims utilization indicated by the filled claim information. In some embodiments, the instructions further cause the processor to assign a therapeutic alternative flag to an alternative drug in response to a generic code number of the alternative drug matching a generic code number of a corresponding requested drug of a respective prior prescription benefit request, and store, in the second database, at least each alternative drug that includes a standard therapeutic class corresponding to a standard therapeutic class of a requested drug of a corresponding prior prescription benefit request.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Implementations of the systems, algorithms, methods, instructions, etc., described herein may be realized in hardware, software, or any combination thereof. The hardware may include, for example, computers, intellectual property (IP) cores, application-specific integrated circuits (ASICs), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

What is claimed is:

1. A system for identifying one or more alternative drugs responsive to a prescription benefits request, the system comprising:
    a processor in communication with a memory including instructions that, when executed by the processor, cause the processor to:
        receive a prescription benefit request, the prescription benefit request indicating at least a requested drug and a patient identifier;
        identify, in a first database, one or more covered alternative drugs based on the requested drug and a drug coverage plan associated with the patient identifier;
        identify, in a second database, one or more additional alternative drugs based on at least one of the requested drug and at least one covered alternative drug of the one or more covered alternative drugs;
        determine, based on the covered drug plan associated with the patient identifier, whether the one or more additional alternative drugs includes at least one covered additional alternative drug;
        in response to a determination that the one or more additional alternative drugs includes at least one covered additional alternative drug, determine, for each of the at least one covered additional alternative drug and the one or more covered alternative drugs, an alternative drug value;
        identify the at least one covered additional alternative drug and the one or more covered alternative drugs having a lowest alternative drug value;
        rank the at least one covered additional alternative drug and the one or more covered alternative drugs having the lowest alternative drug value based on number of times each of the at least one covered additional alternative drug and the one or more covered alternative drugs having the lowest alternative drug value has been filled for an associated prescription;
        generate a request response indicating at least the alternative drug of the at least one covered additional alternative drug and the one or more covered alternative drugs having the lowest alternative drug value ordered according to the rank; and
        communicate an order associated with a prescription request to fill the alternative drug to an order processing device associated with a high-volume pharmacy; and
    a pharmacy fulfillment device that:
        receives, from the order processing device, instructions to fulfill the order;
        identifies a puck having dimensions corresponding to a prescription container of the order;
        controls at least one robotic arm to position the puck on a pallet;
        controls a loading device to load the prescription container into the puck; and
        controls at least one dispensing device to fulfill the order.

2. The system of claim 1, wherein the request response further indicates the alternative drug value associated with the at least one covered additional alternative drug and the one or more covered alternative drugs having the lowest alternative drug value.

3. The system of claim 1, wherein the instructions further cause the processor to determine a dosage and frequency of the at least one covered additional alternative drug and the one or more covered alternative drugs having the lowest alternative drug value based on a dosage and frequency of the requested drug indicated by the prescription benefit request.

4. The system of claim 3, wherein the request response further indicates the dosage and frequency of the at least one covered additional alternative drug and the one or more covered alternative drugs having the lowest alternative drug value.

5. The system of claim 1, wherein the instructions further cause the processor to:
    retrieve prior prescription benefit requests having request dates within a first predetermined period; and
    identify, for each request of the prior prescription benefit requests, alternative drugs filled within a second predetermined period of respective request dates associated with each request of the prior prescription benefit requests.

6. The system of claim 5, wherein the instructions further cause the processor to,
    for each alternative drug filled within the second predetermined period of respective request dates associated with each request of the prior prescription benefit requests that includes a standard therapeutic class corresponding to a standard therapeutic class of a requested drug of a corresponding prior prescription benefit request:
        retrieve filled claim information associated with the corresponding prior prescription benefit requests, wherein the filled claim information indicates the number of times the at least one covered additional alternative drug and the one or more covered alternative drugs having the lowest alternative drug value has been filled.

7. The system of claim 6, wherein the instructions further cause the processor to:
    assign a therapeutic alternative flag to an alternative drug in response to a generic code number of the alternative drug matching a generic code number of a corresponding requested drug of a respective prior prescription benefit request; and
    store, in the second database, at least each alternative drug that includes a standard therapeutic class corresponding to a standard therapeutic class of a requested drug of a corresponding prior prescription benefit request.

8. A method for identifying one or more alternative drugs responsive to a prescription benefits request, the method comprising:
    receiving a prescription benefit request, the prescription benefit request indicating at least a requested drug and a patient identifier;
    identifying, in a first database, one or more covered alternative drugs based on the requested drug and a drug coverage plan associated with the patient identifier;
    identifying, in a second database, one or more additional alternative drugs based on at least one of the requested drug and at least one covered alternative drug of the one or more covered alternative drugs;
    determining, based on the covered drug plan associated with the patient identifier, whether the one or more additional alternative drugs includes at least one covered additional alternative drug;
    in response to a determination that the one or more additional alternative drugs includes at least one covered additional alternative drug, determining, for each of the at least one covered additional alternative drug and the one or more covered alternative drugs, an alternative drug value;

identifying the at least one covered additional alternative drug and the one or more covered alternative drugs having a lowest alternative drug value;

rank the at least one covered additional alternative drug and the one or more covered alternative drugs having the lowest alternative drug value based on number of times each of the at least one covered additional alternative drug and the one or more covered alternative drugs having the lowest alternative drug value has been filled for an associated prescription;

generating a request response indicating at least the alternative drug of the at least one covered additional alternative drug and the one or more covered alternative drugs having the lowest alternative drug value ordered according to the rank;

communicating an order associated with a prescription request to fill the alternative drug to an order processing device associated with a high-volume pharmacy;

receiving, at a pharmacy fulfillment device from the order processing device, instructions to fulfill the order;

identifying, by the pharmacy fulfillment device, a puck having dimensions corresponding to a prescription container of the order;

controlling, by the pharmacy fulfilment device, at least one robotic arm to position the puck on a pallet;

controlling, by the pharmacy fulfillment device, a loading device to load the prescription container into the puck; and controlling, by the pharmacy fulfilment device, at least one dispensing device to fulfill the order.

9. The method of claim 8, wherein the request response further indicates the alternative drug value associated with the at least one covered additional alternative drug and the one or more covered alternative drugs having the lowest alternative drug value.

10. The method of claim 8, further comprising determining a dosage and frequency of the at least one covered additional alternative drug and the one or more covered alternative drugs having the lowest alternative drug value based on a dosage and frequency of the requested drug indicated by the prescription benefit request.

11. The method of claim 10, wherein the request response further indicates the dosage and frequency of the at least one covered additional alternative drug and the one or more covered alternative drugs having the lowest alternative drug value.

12. The method of claim 8, further comprising:
retrieving prior prescription benefit requests having request dates within a first predetermined period; and
identifying, for each request of the prior prescription benefit requests, alternative drugs filled within a second predetermined period of respective request dates associated with each request of the prior prescription benefit requests.

13. The method of claim 12, further comprising, for each alternative drug filled within the second predetermined period of respective request dates associated with each request of the prior prescription benefit requests that includes a standard therapeutic class corresponding to a standard therapeutic class of a requested drug of a corresponding prior prescription benefit request:
retrieving filled claim information associated with the corresponding prior prescription benefit requests the at least one covered additional alternative drug and the one or more covered alternative drugs having the lowest alternative drug value; and.

14. The method of claim 13, further comprising:
assigning a therapeutic alternative flag to an alternative drug in response to a generic code number of the alternative drug matching a generic code number of a corresponding requested drug of a respective prior prescription benefit request; and
storing, in the second database, at least each alternative drug that includes a standard therapeutic class corresponding to a standard therapeutic class of a requested drug of a corresponding prior prescription benefit request.

15. A system for identifying one or more alternative drugs responsive to a prescription benefits request, the system comprising:
a computing device configured to:
receive a prescription benefit request, the prescription benefit request indicating at least a requested drug and a patient identifier;
identify, in a first database, one or more covered alternative drugs based on the requested drug and a drug coverage plan associated with the patient identifier;
identify, in a second database, one or more additional alternative drugs based on at least one of the requested drug and at least one covered alternative drug of the one or more covered alternative drugs;
determine, based on the covered drug plan associated with the patient identifier, whether the one or more additional alternative drugs includes at least one covered additional alternative drug;
in response to a determination that the one or more additional alternative drugs includes at least one covered additional alternative drug, determine, for each of the at least one covered additional alternative drug and the one or more covered alternative drugs, an alternative drug value;
identify the at least one covered additional alternative drug and the one or more covered alternative drugs having a lowest alternative drug value;
determine a dosage and frequency of the at least one covered additional alternative drug and the one or more covered alternative drugs having the lowest alternative drug value based on a dosage and frequency of the requested drug indicated by the prescription benefit request;
rank the at least one covered additional alternative drug and the one or more covered alternative drugs having the lowest alternative drug value based on number of times each of the at least one covered additional alternative drug and the one or more covered alternative drugs having the lowest alternative drug value has been filled for an associated prescription;
generate a request response indicating at least the alternative drug of the at least one covered additional alternative drug and the one or more covered alternative drugs having the lowest alternative drug value, the alternative drug value associated with the at least one covered additional alternative drug and the one or more covered alternative drugs having the lowest alternative drug value, and the dosage and frequency of the at least one covered additional alternative drug and the one or more covered alternative drugs having the lowest alternative drug value, wherein the request response is ordered according to the rank; and communicate an order associated with a prescription request to fill the alternative drug to an order processing device associated with a high-volume pharmacy; and a pharmacy fulfillment device that:
- receives, from the order processing device, instructions to fulfill the order;
- identifies a puck having dimensions corresponding to a prescription container of the order;
- controls at least one robotic arm to position the puck on a pallet;
- controls a loading device to load the prescription container into the puck; and
- controls at least one dispensing device to fulfill the order.

16. The system of claim 15, wherein the computing device is further configured to:
- retrieve prior prescription benefit requests having request dates within a first predetermined period; and
- identify, for each request of the prior prescription benefit requests, alternative drugs filled within a second predetermined period of respective request dates associated with each request of the prior prescription benefit requests.

17. The system of claim 16, wherein the computing device is further configured to, for each alternative drug filled within the second predetermined period of respective request dates associated with each request of the prior prescription that includes a standard therapeutic class corresponding to a standard therapeutic class of a requested drug of a corresponding prior prescription benefit request:
- retrieve filled claim information associated with the corresponding prior prescription benefit requests the at least one covered additional alternative drug and the one or more covered alternative drugs having the lowest alternative drug value.

18. The system of claim 17, wherein the computing device is further configured to:
- assign a therapeutic alternative flag to an alternative drug in response to a generic code number of the alternative drug matching a generic code number of a corresponding requested drug of a respective prior prescription benefit request; and
- store, in the second database, at least each alternative drug that includes a standard therapeutic class corresponding to a standard therapeutic class of a requested drug of a corresponding prior prescription benefit request.

* * * * *